US00PP29003P2

(12) United States Plant Patent
Hofmann

(10) Patent No.: US PP29,003 P2
(45) Date of Patent: Feb. 27, 2018

(54) ***MANDEVILLA* PLANT NAMED 'INMANREDGRAN'**

(50) Latin Name: *Mandevilla hybrida*
Varietal Denomination: Inmanredgran

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 15/330,326

(22) Filed: Sep. 6, 2016

(51) Int. Cl.
*A01H 5/02* (2006.01)

(52) U.S. Cl.
USPC ..... Plt./232

(58) Field of Classification Search
USPC ..... Plt./232
See application file for complete search history.

(56) References Cited

PUBLICATIONS

UPOV hit on *Mandevilla* plant named 'Inmanredgran', QZ PBR 20161662, filed Jul. 1, 2016.*

* cited by examiner

*Primary Examiner* — Anne M Grunberg
(74) *Attorney, Agent, or Firm* — C. A. Whealy

(57) ABSTRACT

A new and distinct cultivar of *Mandevilla* plant named 'Inmanredgran', characterized by its upright and vining plant habit; strong and moderately vigorous growth habit; freely branching habit; glossy dark green-colored leaves; freely flowering habit; and large red-colored flowers that resist fading.

2 Drawing Sheets

Botanical designation: *Mandevilla hybrida.*
Cultivar denomination: 'INMANREDGRAN'.

BACKGROUND OF THE INVENTION

The present invention relates to a new and distinct cultivar of *Mandevilla* plant, botanically known as *Mandevilla hybrida* and hereinafter referred to by the name 'Inmanredgran'.

The new *Mandevilla* plant is a product of a planned breeding program conducted by the Inventor in Johannesburg, South Africa and Heidesheim, Germany. The objective of the breeding program is to create new strong and freely branching *Mandevilla* plants that flower freely and have large attractive flowers that resist fading.

The new *Mandevilla* plant originated from a cross-pollination conducted by the Inventor in Johannesburg, South Africa in November, 2010 of a proprietary selection of *Mandevilla hybrida* identified as code number D09-1067-15, not patented, as the female, or seed parent with a proprietary selection of *Mandevilla hybrida* identified as code number D09-1067-3, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2012.

Asexual reproduction of the new *Mandevilla* plant by cuttings in a controlled greenhouse environment in Heidesheim, Germany, since June, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanredgran'. These characteristics in combination distinguish 'Inmanredgran' as a new and distinct *Mandevilla* plant:

1. Upright and vining plant habit.
2. Strong and moderately vigorous growth habit.
3. Freely branching habit.
4. Glossy dark green-colored leaves.
5. Freely flowering habit.
6. Large red-colored flowers that resist fading.

Plants of the new *Mandevilla* can be compared to plants of the female parent selection. Plants of the new *Mandevilla* differ primarily from plants of the female parent selection in the following characteristics:

1. Plants of the new *Mandevilla* are not as freely branching as plants of the female parent selection.
2. Plants of the new *Mandevilla* have smaller leaves than plants of the female parent selection.
3. Plants of the new *Mandevilla* have larger flowers than plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* have larger and lighter green-colored leaves than plants of the male parent selection.

2. Plants of the new *Mandevilla* flower earlier than plants of the male parent selection.
3. Plants of the new *Mandevilla* have larger flowers than plants of the male parent selection.

Plants of the new *Mandevilla* can also be compared to plants of *Mandevilla hybrida* 'Lanlouisiana', disclosed in U.S. Plant Pat. No. 25,873. In side-by-side comparisons plants of the new *Mandevilla* differ primarily from plants 'Lanlouisiana' in the following characteristics:

1. Plants of the new *Mandevilla* are more freely branching than plants of 'Lanlouisiana'.
2. Plants of the new *Mandevilla* have smaller leaves than plants of 'Lanlouisiana'.
3. Flowers of plants of the new *Mandevilla* are more open and larger than flowers of plants of 'Lanlouisiana'.

Plants of the new *Mandevilla* can also be compared to plants of *Mandevilla sanderi* 'Rio Red', not patented. In side-by-side comparisons plants of the new *Mandevilla* differ primarily from plants 'Rio Red' in the following characteristics:

1. Plants of the new *Mandevilla* are larger and stronger than plants of 'Rio Red'.
2. Plants of the new *Mandevilla* have larger leaves than plants of 'Rio Red'.
3. Plants of the new *Mandevilla* have larger flowers than plants of 'Rio Red'.
4. Flower color of plants of the new *Mandevilla* does not fade whereas flower color of plants of 'Rio Red' fades.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanredgran' grown in a container.

The photograph on the second sheet is a close-up view of a typical flowering plant of 'Inmanredgran'.

DETAILED BOTANICAL DESCRIPTION

The aforementioned photographs and following observations, measurements and values describe plants grown during the late spring and early summer in 9.5-cm containers in a polyethylene-covered greenhouse in Almeria, Spain and under cultural practices typical of *Mandevilla* commercial production. During the production of the plants, day temperatures ranged from 20° C. to 35° C. and night temperatures ranged from 20° C. to 25° C. Plants were 15 weeks old when the photographs and description were taken. In the following description, color references are made to The Royal Horticultural Society Colour Chart, 2015 Edition, except where general terms of ordinary dictionary significance are used.

Botanical classification: *Mandevilla hybrida* 'Inmanredgran'.

Parentage:

*Female, or seed, parent*.—Proprietary selection of *Mandevilla hybrida* identified as code number D09-1067-15.

*Male, or pollen, parent*.—Proprietary selection of *Mandevilla hybrida* identified as code number D09-1067-3.

Propagation:

*Type*.—By vegetative cuttings.

*Time to initiate roots, summer*.—About 24 days at temperatures ranging from 20° C. to 35° C.

*Time to initiate roots, winter*.—About 28 to 30 days at temperatures ranging from 20° C. to 25° C.

*Time to produce a rooted young plant, summer*.—About 26 days at temperatures ranging from 20° C. to 35° C.

*Time to produce a rooted young plant, winter*.—About 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Upright and vining plant habit; moderately vigorous growth habit.

*Plant height*.—About 54.3 cm.

*Plant diameter* (*spread*).—About 40.9 cm.

*Lateral branch description*.—Branching habit: Freely branching habit with about six lateral branches and about six secondary branches developing per plant; pinching enhances lateral branch development. Length: About 27.4 cm. Diameter: About 3 mm. Internode length: About 5.7 cm. Strength: Strong. Texture and luster: Smooth, glabrous; glossy; becoming woody with development. Color, developing: Close to between 143B and 144A. Color, developed: Close to 144A; when woody, close to between N199D to 200D.

Leaf description:

*Arrangement*.—Opposite, simple.

*Length*.—About 7.6 cm.

*Width*.—About 5.2 cm.

*Shape*.—Broadly ovate to oblong.

*Apex*.—Short apiculate.

*Base*.—Obtuse to truncate.

*Margin*.—Entire.

*Texture and luster, upper surface*.—Smooth, glabrous; glossy.

*Texture and luster, lower surface*.—Smooth, glabrous; slightly glossy.

*Venation pattern*.—Pinnate.

*Color*.—Developing leaves, upper surface: Slightly darker than 143A. Developing leaves, lower surface: Close to 146B. Full expanded leaves, upper surface: Darker than between NN137A and 147A; venation, close to 143A. Fully expanded leaves, lower surface: Close to 146B; venation, close to 144C.

*Petioles*.—Length: About 1.4 cm. Diameter: About 2 mm. Strength: Moderately strong. Texture and luster, upper and lower surfaces: Smooth, glabrous; slightly glossy. Color, upper surface: Close to 144B. Color, lower surface: Close to 144C.

Flower description:

*Flower type and flowering habit*.—Single salverform flowers arranged in axillary cymes; flowers star-shaped and face mostly outwardly; freely flowering habit with about five flowers developing per inflorescence and about 70 flowers developing per plant during the flowering season.

*Natural flowering season*.—Plants flower continuously from spring into the autumn in Spain.

*Flower longevity on the plant*.—About ten days; flowers not persistent.

*Fragrance*.—Faint; sweetly acidic, pleasant.

*Inflorescence height*.—About 11.5 cm.

*Inflorescence diameter*.—About 13.2 cm.

*Flower buds*.—Length: About 5.3 cm. Diameter: About 1 cm. Shape: Narrowly oblanceolate. Texture and luster: Smooth, glabrous; slightly glossy. Color: Close to 56A; towards the base, close to 145A and 145B.

*Flowers*.—Appearance: Flared trumpet, corolla fused and five-parted. Diameter: Large, about 9.9 cm. Depth (length): About 7.3 cm. Throat diameter: About 1.7 cm. Tube length: About 4.9 cm. Tube diameter: Proximally, about 5 mm; distally, about 1.9 cm.

*Corolla*.—Quantity and arrangement: Five petals arranged in a single whorl; lower 48.5% portion of the petals are fused into a tube. Petal length: About 10.5 cm. Petal width: About 4.4 cm. Petal shape and appearance: Roughly spatulate. Petal apex: Apiculate to acute. Petal margin: Entire; slightly undulate. Petal texture and luster, upper surface: Smooth, glabrous; velvety; matte. Petal texture and luster, lower surface: Smooth, glabrous; velvety; moderately glossy. Throat and tube texture: Smooth, glabrous. Color: Petal, when opening, upper surface: Darker and more intense than N45A. Petal, when opening, lower surface: Close to between 53A and 185A. Petal, fully opened, upper surface: Darker and more intense than 46A; venation, similar to lamina; color does not fade with development. Petal, fully opened, lower surface: Close to between 53A and 185A; color does not fade with development. Throat: Close to 53A to 53B; venation, close to 25B becoming closer to 15A to 15B with development. Tube: Close to N144D; venation, close to N144D.

*Corona*.—Quantity and arrangement: Five sepals arranged in a single whorl. Sepal length: About 9 mm. Sepal width: About 3 mm. Sepal shape: Narrowly deltoid. Sepal apex: Narrowly acute. Sepal base: Broadly cuneate. Sepal margin: Entire. Sepal texture and luster, upper surface: Smooth, glabrous; glossy. Sepal texture and luster, lower surface: Smooth, glabrous; matte.

*Sepal color*.—Immature, upper and lower surfaces: Close to 145B; at the apex, close to 179A. Mature, upper and lower surfaces: Close to 145B to 145C.

*Peduncles*.—Length: About 5.8 cm. Diameter: About 2 mm. Strength: Strong. Aspect: About 30° from lateral branch axis. Texture and luster: Smooth, glabrous; glossy. Color: Close to 143C.

*Pedicels*.—Length: About 2.3 cm. Diameter: About 2 mm. Strength: Strong. Aspect: About 40° from peduncle axis. Texture and luster: Smooth, glabrous; moderately glossy. Color: Close to 144B.

*Reproductive organs*.—Stamens: Quantity and arrangement: Typically five; basifixed; anthers connivent. Filament length: About 1 mm. Filament color: Close to 151D. Anther shape: Narrowly oblong. Anther size: About 9 mm by 1.5 mm. Anther color: Close to 160C. Pollen amount: None observed. Pistils: Quantity: Typically one. Pistil length: About 2.3 cm. Style length: About 1.85 cm. Style color: Close to 145D. Stigma diameter: About 2 mm. Stigma shape: Club-shaped. Stigma color: Close to 146C. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be suitable for USDA Hardiness Zones 9 to 13.

It is claimed:

1. A new and distinct *Mandevilla* plant named 'Inmanredgran' as illustrated and described.

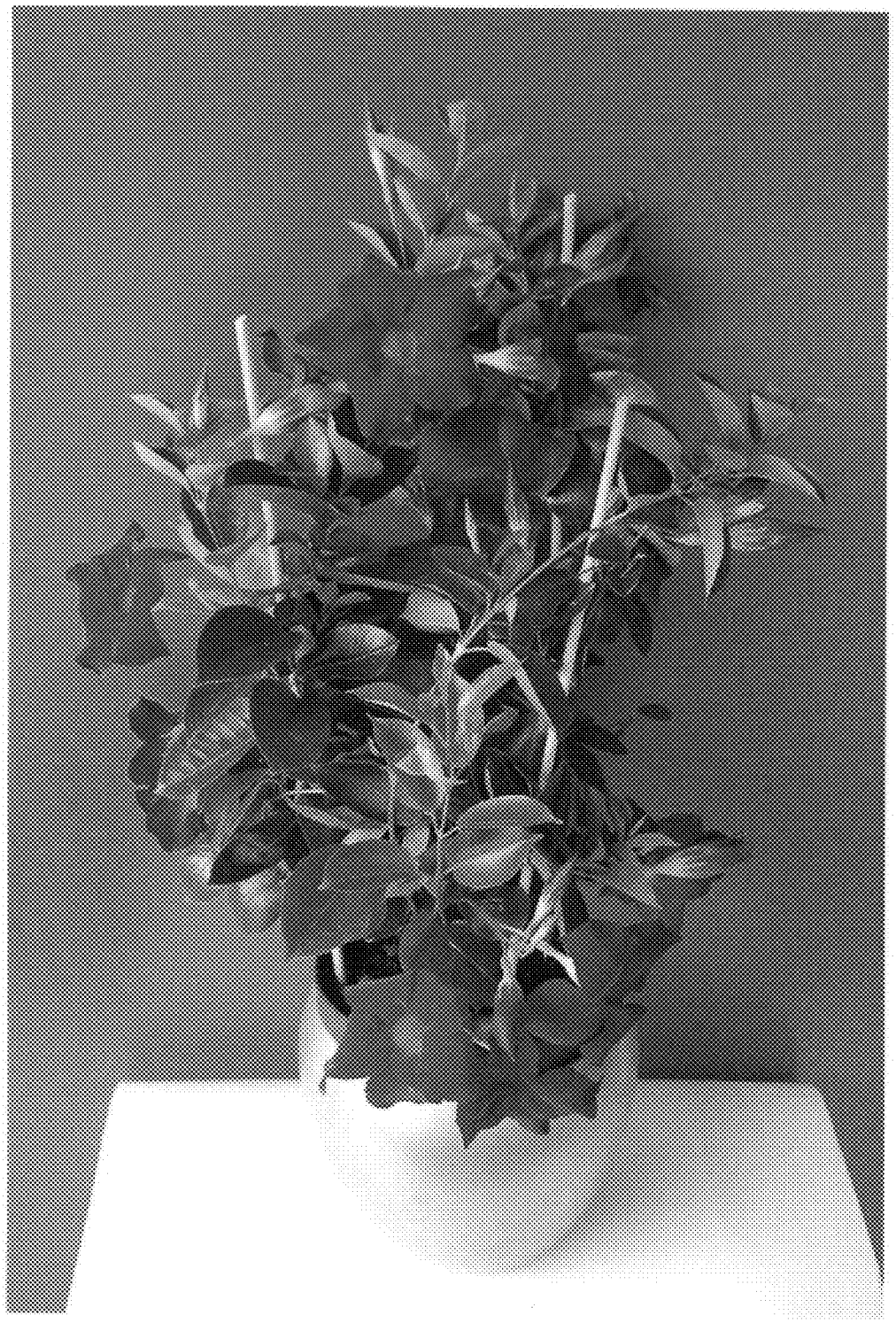

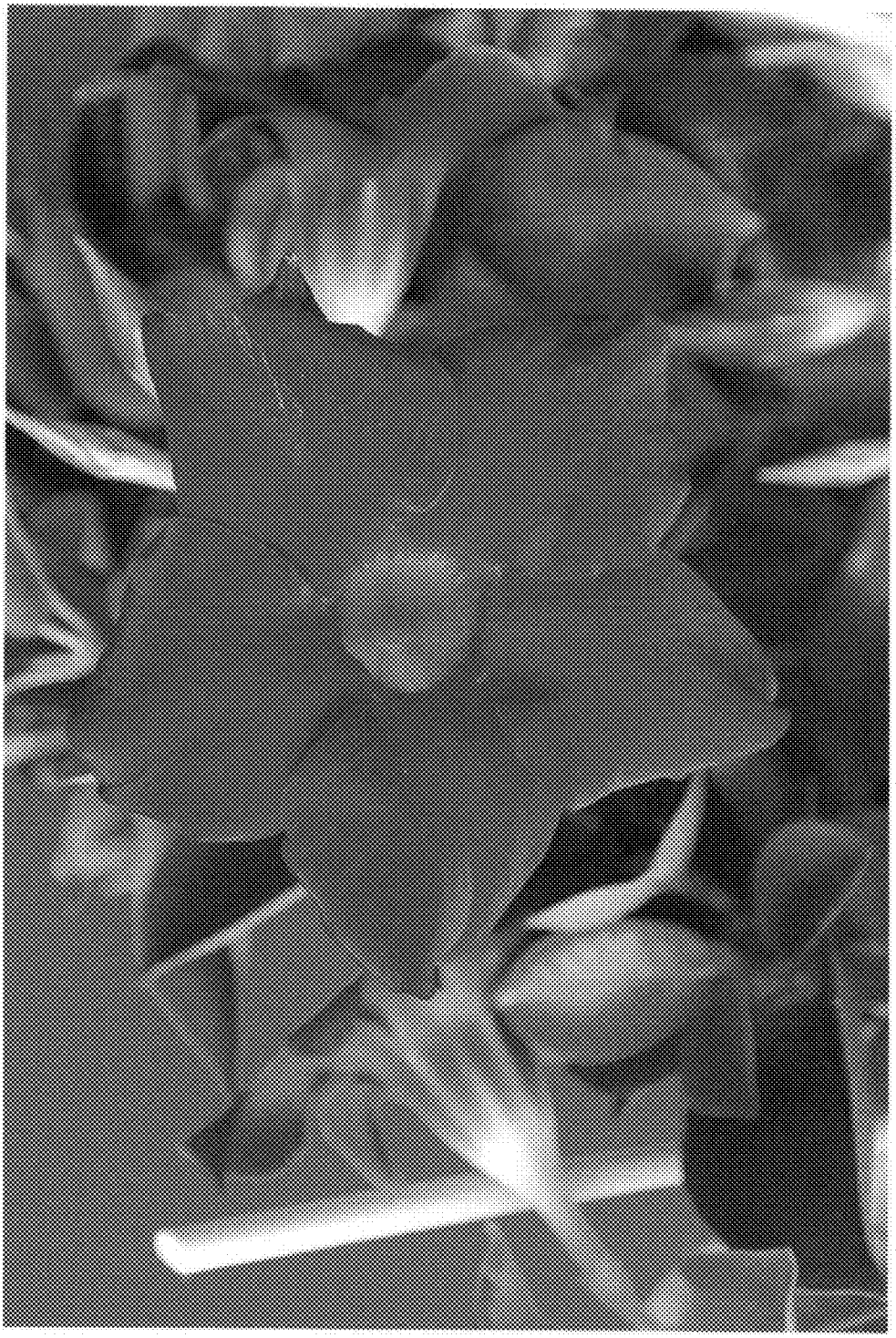

* * * * *